United States Patent [19]

Mendicino

[11] Patent Number: 4,727,173
[45] Date of Patent: Feb. 23, 1988

[54] PROCESS FOR PRODUCING TRIALKOXYSILANES FROM THE REACTION OF SILICON METAL AND ALCOHOL

[75] Inventor: Frank D. Mendicino, Marietta, Ohio

[73] Assignee: Union Carbide Corporation, Danbury, Conn.

[21] Appl. No.: 33,017

[22] Filed: Mar. 31, 1987

[51] Int. Cl.$^4$ .................................................. C07F 7/04
[52] U.S. Cl. ........................................................ 556/470
[58] Field of Search ........................................... 556/470

[56] References Cited

U.S. PATENT DOCUMENTS

| | | | |
|---|---|---|---|
| 2,473,260 | 6/1949 | Rochow | 260/448.8 |
| 3,072,700 | 1/1963 | de Wit | 260/448.8 |
| 3,641,077 | 2/1972 | Rochow | 260/448.8 |
| 3,775,547 | 11/1973 | Mursoka et al. | 260/448.8 |
| 4,185,029 | 1/1980 | Kreuzburg | 556/470 |
| 4,289,889 | 9/1981 | Herdle et al. | 556/470 |
| 4,447,632 | 5/1984 | Mallon | 556/470 |
| 4,487,949 | 12/1984 | Mallon | 556/470 |

FOREIGN PATENT DOCUMENTS

| | | | |
|---|---|---|---|
| 163529 | 3/1979 | Japan | 556/470 |
| 28928 | of 1980 | Japan | 556/470 |
| 33457 | 3/1980 | Japan | 556/470 |
| 72198 | 5/1980 | Japan | 556/470 |
| 72197 | 5/1980 | Japan | 556/470 |
| 28929 | 6/1980 | Japan | 556/470 |
| 2641 | 7/1980 | Japan | 556/470 |
| 11538 | 11/1980 | Japan | 556/470 |
| 16492 | of 1981 | Japan | 556/470 |

*Primary Examiner*—Paul F. Shaver
*Attorney, Agent, or Firm*—Paul W. Leuzzi

[57] ABSTRACT

A process for producing trialkoxysilane by the direct reaction of silicon metal with an alcohol, ROH, in the presence of a catalytically effective amount of copper (II) hydroxide, wherein R is an alkyl group containing from 1 to 6 carbon atoms.

19 Claims, No Drawings

PROCESS FOR PRODUCING TRIALKOXYSILANES FROM THE REACTION OF SILICON METAL AND ALCOHOL

FIELD OF THE INVENTION

The inventive process generally relates to the production of trialkoxysilanes in the catalyzed reaction of silicon metal with alcohol. In particular, the process entails the reaction of silicon metal and alcohol in the presence of a copper (II) hydroxide catalyst. The process exhibits a high selectivity for trialkoxysilane in that the ratio of trialkoxysilane to tetra-alkoxysilane produced is high.

BACKGROUND OF THE INVENTION

Trialkoxysilanes are used in the production of silane coupling agents. U.S. Pat. No. 3,641,077 teaches the preparation of trialkoxysilanes by directly reacting silicon metal with alcohol in the presence of a catalyst produced by sintering copper and silicon. However, this method results in low yields of trialkoxysilanes.

U.S. Pat. No. 3,775,457 teaches the production of alkoxysilanes from the reaction of an alcohol and finely divided silicon metal in the presence of a cuprous chloride catalyst. Although the use of cuprous chloride results in increased yield over that obtained using the sintered copper-silicon catalyst, the use of cuprous chloride catalyst also results in the formation of HCl which in turn necessitates the use of costly corosion resistant materials of construction for the reactor. Further, the presence of chloride in the reactor and in the product stream reduces the yield of trialkoxysilane by catalyzing the further reaction of trialkoxysilane with the alcohol to yield tetra-alkoxysilane. Also, when methanol is a reactant, the HCl resulting from the use of the cuprous chloride catalyst will react with some of the methanol to produce methyl chloride and water. This makes the cuprous chloride catalyzed reaction inefficient through the loss of methanol and the water can react with trialkoxysilanes to produce siloxanes. The presence of water in the reaction mixture can also inhibit the conversion of silicon metal.

Thus, there continues to exist the need for a process of directly reacting silicon metal and an alcohol to obtain trialkoxysilanes which process has increased yields of triakloxysilanes and yet avoids the above-mentioned deficiencies of the cuprous chloride process.

OBJECTS OF THE INVENTION

It is therefore an object of the invention to provide a process for producing trialkoxysilane from silicon metal and alcohol which results in a high trialkoxysilane to tetra-alkoxysilane ratio in the product.

Another object of the invention is to provide such a process which results in a high conversion of silicon metal into trialkoxysilane product and which results in little unreacted silicon content in the reaction residue.

A further object of the invention is to provide such a process which does not require the use of costly corrosion resistant materials in the construction of the process apparatus.

SUMMARY OF THE INVENTION

The present invention provides a process for producing trialkoxysilane of the formula $HSi(OR)_3$ wherein R is an alkyl group containing from 1 to 6 carbon atoms inclusive, which process comprises:

(a) forming a reaction mixture comprising an alcohol of the formula ROH, an inert solvent, silicon metal, and a catalytically effective amount of copper (II) hydroxide; and (b) reacting said alcohol with said silicon metal to produce trialkoxysilane.

The process of this invention produces trialkoxysilanes in high yield with ratios of trialkoxysilane to tetra-alkoxysilanes of greater than about 9 to 1 (on a weight basis). Furthermore, the use of copper (II) hydroxide does not generate corrosive materials and thus costly materials of construction are not required for the reactor. The process of the invention also results in high silicon conversion.

DETAILED DESCRIPTION OF THE INVENTION

Catalyst

The copper (II) hydroxide catalyst used in the process of this invention is present in an amount effective to catalyze the reaction. Generally an effective amount ranges from about 0.01 to about 5 parts by weight of catalyst per 100 parts by weight of the silicon metal. Usually the amount of copper (II) hydroxide will be from about 0.1 to about 2.6 parts by weight per 100 parts by of the weight silicon metal. The preferred amount of copper (II) hydroxide catalyst is from about 0.1 to about 0.7 parts by weight per 100 parts by weight silicon metal.

Silicon

The silicon metal reactant used in the process of this invention can generally be any commercially available grade of silicon in particulate form. A typical composition of commercial silicon metal useful in this invention, expressed in percent by weight, is Silicon—98.5%; Iron—less than 0.50%; Aluminum—0.20 to 0.35%; Calcium—0.02 to 0.10%; Water—less than 0.1%; Lead—less than 10 ppm; Boron—less than 20 ppm. Generally smaller particle size (less than about 50 mesh) is preferred for ease of processing. Sieving of ground silicon to regulate particle size is optional.

The presence of tin in the reaction has adverse effects on the reaction rate and/or the selectivity for trialkoxysilane and so should be avoided (e.g. amounts as low as 75 parts per million show an adverse effect on the reaction).

Alcohol

The alcohols which are useful in the process of this invention are those of the formula ROH wherein R is an alkyl group containing from 1 to 6 carbon atoms, inclusive. Preferably R is an alkyl group containing from 1 to 3 carbon atoms inclusive. The most preferred alcohols are methanol and ethanol.

The silicon metal, catalyst and solvent can be added together in any order. Generally, the reaction is run in a slurry and the alcohol is fed into the slurry as a gas or liquid. The reaction typically displays a one to two hour induction period. The initial alchohol feed rate is therefore low and is brought up as the reaction progresses. Generally, once the reaction is running, the alcohol feed rate can be adjusted to give the desired level of methanol conversion. One skilled in the art can readily adjust the feed rate in a given reaction run by monitoring the product composition. If the feed rate is too high the product stream will contain a larger proportion of unreacted alcohol.

Solvent

The solvents useful in the process of this invention are inert solvents that do not degrade under the reaction conditions. The preferred solvents are high temperature stable organic solvents such as Therminol ® 59, 60 and Therminol ® 66, diphenyl ether and dodecylbenzene. THERMINOL ® is the Monsanto Company trade name for heat transfer fluids. THERMINOL ® 60 is a polyaromatic compound with an average molecular weight of 250. Its optimum temperature range is from −45° to 315° C. THERMINOL ® 66 is a modified terphenyl with an average molecular weight of 240. It has a higher upper temperature limit than the THERMINOL ® 60: its maximum upper temperature limit is 371° C. The solvent is present in an amount sufficient to disperse the reactants homogeneously.

Reaction Conditions

The reaction is generally conducted at temperatures above about 150° C. but below such a temperature as would degrade or decompose the reactants or solvents. Preferably the reaction temperature is maintained in a range from about 200° C. to about 240° C. The reaction could of course be run at higher temperatures although at no particular advantage.

The pressure at which the reaction is conducted is not critical and can be varied from subatmospheric to superatmospheric. The reaction is generally run at about atmospheric pressure.

Preferably the contents of the reaction mixture are agitated to maintain a well mixed slurry of the silicon particles and alcohol in the solvent. The reaction mixture is preferably well insulated to assure that the trialkoxysilane does not reflux. Refluxing could encourage further reaction of the trialkoxysilane with the alcohol, resulting in loss of the desired trialkoxysilane product by the formation of tetramethoxysilane.

Recovery

When methanol is the alcohol feed, the recovery of the trimethoxysilane product from the crude product is difficult since the the methanol and trimethoxysilane form a minimum boiling azeotrope containing about 54% methanol. If the crude product is recycled to the reactor with the trimethoxysilane unremoved, the trimethoxysilane will likely react further with the methanol to produce tetramethoxysilane. It has been found that tetramethoxysilane can be used to extract the trimethoxysilane from the methanol/trimethoxysilane azeotrope. When tetramethoxysilane is added to the methanol/trimethoxysilane azeotrope in a continuous distillation operation the methanol can be distilled off while the trimethoxysilane remains behind with the tetraamethoxysilane. This distillation/recovery process uses tetramethoxysilane which is produced as a by product of the reaction between the silicon and the alcohol to recover the desired trimethoxysilane from the azeotrope in high purity and efficiency. Using tetramethoxysilane as the extractant minimizes cost and separating difficulty since no new material need be introduced into the system.

The above described extractive distillation can for example be conducted in two continuous distillation columns. The first column serves as the extractive column, where tetramethoxysilane is added near the top of the column thus flowing downward to contact the azeotrope, thus allowing the methanol to be distilled off (overhead) from the trimethoxysilane and tetramethoxysilane (bottoms). In the second column trimethoxysilane can be distilled off (overhead) from the tetramethoxysilane (bottoms). The tetramethoxysilane can be collected near the bottom of the second column and be recycled to the top of the first column.

Whereas the scope of the instant invention is set forth in the appended claims, the following specific examples are set forth for illustration only and are not to be construed as limiting the scope of the invention.

EXAMPLES

A 1000 milliliter four neck flask was charged with 50 grams of silicon metal, 100 cc of THERMINOL ® 60, a high boiling inert solvent, and copper (II) hydroxide catalyst. Alcohol was added either via a gravity feed constant addition funnel or through an FMI ® pump and flow was controlled using a micrometer adjustment. The reaction temperature was controlled using a thermometer and an I$^2$R ® Thermo-O-Watch. The reactants were agitated using a mechanical stirrer, i.e. an air motor, with a teflon blade and glass shaft. A short (about 12″) Vigreux column was used to stop entrainment of the solvent. Product samples were removed at time intervals through a distillation head with a nitrogen blow by and collected in a 250 milliliter receiver. The product cuts or samples were taken on a 0.5-2 hour basis and 2 to 5 gram samples were submitted in pressure bottles for gas chromatographic analysis. The reaction was run at 220° C. until no more silicon metal was converted to volatile products.

TABLES

The Table numbers correspond to Example numbers.

The column headings in the following tables have the following meanings:

SAMPLE TAKEN—Weight of the Sample collected in grams

RX TIME—Reaction time interval since previous sample (minutes)

METHANOL FEED(GM)—Weight of the methanol fed between samples (grams)

MEOH—Weight % methanol in sample determined by gas chromatograph analysis

TRI—Weight % trialkoxysilane product in sample determined by gas chromatograph analysis TETR—Weight % tetramethoxysilane by gas chromatograph analysis SILOXANES—Weight % total di-siloxane compounds (Tetra Tetra, Tri-Tri and Tetra-Tri)

SOL—Weight % Solvent in sample determined by gas chromatograph analysis

The data shown under the above listed column headings were used to calculate the entries under the below listed column headings.

METHANOL RATE (GM/H)—Methanol feed rate (grams/hour).

Si IN POT (GM)—Unreacted silicon metal remaining in the pot before each sample (grams).

Si/SAMPLE TOTAL (GM)—Total silicon present in each sample (grams).

Si/SAMPLE RATE (GM/H)—Rate of silicon production in each sample (grams/hour).

SELECTIVITY/SAMPLE—Selectivity for each sample (ratio of trimethoxysilane to tetramethoxysilane (by weight)).

SELECTIVITY/CUM—Cumulative selectivity after each sample. (Ratio of trimethoxysilane to tetramethoxysilane produced from beginning of reaction to time of sample)

EXAMPLE 1

In this example 1.3 grams of copper (II) hydroxide catalyst was employed, the silicon metal was 65×150 mesh particles.

An air motor provided agitation of the reactants.

Samples were taken at time intervals as shown. As can be seen from the data on Table I, below the ratio of trimethoxysilane to tetramethoxysilane produced is good, approximately 7 to 1.

This represents an 80.4 mole percent conversion of the silicon metal to trimethoxysilane. In contrast, only 10 mole percent of the silicon metal was converted to tetramethoxysilane.

EXAMPLES 2 THROUGH 5

Examples 2 through 5 were run in the manner described for Example 1 except that the amount of copper (II) hydroxide catalyst was varied as shown, below. Examples 3, 4 and 5 demonstrate that the solvent can be reused in subsequent runs of the process.

EXAMPLE 2

In this example 0.65 grams of copper (II) hydroxide was employed, the silicon metal was 65×150 mesh particles. An air motor provided agitation of the reactants.

This run showed an 82.6 mole percent conversion of the silicon metal to trimethoxysilane. In contrast, only 9.3 mole percent of the silicon metal was converted to tetramethoxysilane.

EXAMPLE 3

In this example, 0.65 grams of copper (II) hydroxide was employed, the silicon metal was 65×150 mesh particles. Solvent from a previous experiment was recycled, (77.5 grams) and 22.5 grams of unused solvent was added to give 100 grams of solvent. This run showed an 82.9 mole percent conversion of the silicon metal to trimethoxysilane. In contrast, only 9.4 mole percent of the silicon metal was converted to tetramethoxysilane.

TABLE 2

| SAMPLE NO. | SAMPLE SIZE (GM) | SAMPLE INTERVAL TIME (MIN) | METHANOL FEED (GM) | METHANOL RATE (GM/H) | GC ANALYSIS (%) MEOH | TRI | TETR | SILOXANES | SOL | Si IN POT (GM) | Si/SAMPLE TOTAL (GM) | Si/SAMPLE RATE (GM/H) | SELECTIVITY SAMPLE | SELECTIVITY CUM |
|---|---|---|---|---|---|---|---|---|---|---|---|---|---|---|
| 2a | 42.3 | 60 | 47.5 | 47.5 | 89.1 | 4.0 | 0.7 | 2.3 | 4.0 | 50.00 | 0.67 | 0.7 | 5.7 | 5.7 |
| 2b | 45.5 | 60 | 47.5 | 47.5 | 44.4 | 52.1 | 2.5 | 0.6 | 0.3 | 49.33 | 5.71 | 5.7 | 20.8 | 17.7 |
| 2c | 46.2 | 60 | 43.5 | 43.5 | 30.9 | 59.2 | 9.0 | 0.9 | 0.1 | 43.62 | 7.14 | 7.1 | 6.6 | 9.4 |
| 2d | 45.9 | 60 | 47.5 | 47.5 | 35.5 | 55.0 | 8.4 | 1.0 | 0.1 | 36.48 | 6.61 | 6.6 | 6.5 | 8.3 |
| 2e | 94.4 | 120 | 95.0 | 47.5 | 37.3 | 50.0 | 11.8 | 0.9 | 0.0 | 29.87 | 13.08 | 6.5 | 4.2 | 6.1 |
| 2f | 90.4 | 120 | 95.0 | 47.5 | 53.6 | 42.1 | 3.4 | 0.8 | 0.1 | 16.79 | 9.47 | 4.7 | 12.4 | 6.9 |
| 2g | 89.9 | 120 | 87.1 | 43.6 | 80.4 | 17.8 | 1.0 | 0.8 | 0.0 | 7.33 | 4.00 | 2.0 | 17.8 | 7.3 |
| 2h | 21.6 | 30 | 23.7 | 47.4 | 88.6 | 2.8 | 3.4 | 1.2 | 4.0 | 3.32 | 0.33 | 0.7 | 0.8 | 7.1 |

TABLE 1

| SAMPLE NO. | SAMPLE SIZE (GM) | SAMPLE INTERVAL (MIN) | METHANOL FEED (GM) | METHANOL RATE (GM/H) | PRODUCT GC ANALYSIS (%) MEOH | TRI | TETR | SILOXANES | SOL | Si IN POT (GM) | Si/SAMPLE TOTAL (GM) | Si/SAMPLE RATE (GM/H) | SELECTIVITY SAMPLE | SELECTIVITY CUM |
|---|---|---|---|---|---|---|---|---|---|---|---|---|---|---|
| 1a | 45.7 | 60 | 49.1 | 49.1 | 97.4 | 0.2 | 0.1 | 0.2 | 2.1 | 50.00 | 0.05 | 0.01 | 2.0 | 2.0 |
| 1b | 46.3 | 60 | 46.7 | 46.7 | 38.9 | 52.6 | 8.0 | 0.5 | 0.0 | 49.95 | 6.32 | 6.3 | 6.6 | 6.5 |
| 1c | 44.5 | 60 | 41.9 | 41.9 | 27.1 | 64.2 | 7.8 | 0.8 | 0.0 | 43.62 | 7.28 | 7.3 | 8.2 | 7.3 |
| 1d | 54.3 | 85 | 51.4 | 36.3 | 23.3 | 68.9 | 6.8 | 1.0 | 0.0 | 36.35 | 9.39 | 6.6 | 10.1 | 8.3 |
| 1e | 71.7 | 120 | 68.9 | 34.5 | 34.0 | 57.5 | 7.5 | 1.1 | 0.0 | 26.96 | 10.63 | 5.3 | 7.7 | 8.1 |
| 1f | 102.4 | 130 | 97.3 | 44.9 | 59.7 | 32.1 | 7.3 | 0.7 | 0.1 | 16.32 | 9.09 | 4.2 | 4.4 | 6.9 |
| 1g | 42.9 | 60 | 40.4 | 40.4 | 80.3 | 14.0 | 4.8 | 1.1 | 0.0 | 7.24 | 1.87 | 1.9 | 2.9 | 6.6 |
| 1h | 109.6 | 120 | 108.4 | 54.2 | 93.4 | 4.2 | 1.0 | 0.7 | 0.6 | 5.37 | 1.43 | 0.7 | 4.2 | 6.5 |

TABLE 3

| SAMPLE NO. | SAMPLE SIZE (GM) | RX TIME (MIN) | METHANOL FEED (GM) | METHANOL RATE (GM/H) | GC ANALYSIS (%) MEOH | TRI | TETR | SILOXANES | SOL | Si IN POT (GM) | Si/SAMPLE TOTAL (GM) | Si/SAMPLE RATE (GM/H) | SELECTIVITY SAMPLE | SELECTIVITY CUM |
|---|---|---|---|---|---|---|---|---|---|---|---|---|---|---|
| 3a | 43.0 | 60 | 47.5 | 47.5 | 94.6 | 1.0 | 0.9 | 0.4 | 3.2 | 50.00 | 0.20 | 0.2 | 1.1 | 1.1 |
| 3b | 47.5 | 60 | 47.5 | 47.5 | 52.3 | 39.1 | 7.8 | 0.5 | 0.3 | 49.80 | 5.00 | 5.0 | 5.0 | 4.7 |
| 3c | 96.9 | 120 | 95.0 | 47.5 | 38.1 | 56.9 | 4.4 | 0.6 | 0.1 | 44.80 | 13.57 | 6.8 | 12.9 | 8.9 |
| 3d | 74.3 | 92 | 71.2 | 46.4 | 37.5 | 48.1 | 13.7 | 0.7 | 0.1 | 31.22 | 10.20 | 6.6 | 3.5 | 5.9 |
| 3e | 56.3 | 71 | 56.2 | 47.5 | 54.3 | 39.1 | 4.7 | 1.3 | 0.7 | 21.03 | 5.71 | 4.8 | 8.3 | 6.2 |
| 3f | 48.1 | 60 | 43.5 | 43.5 | 58.5 | 35.3 | 3.7 | 2.4 | 0.2 | 15.32 | 4.49 | 4.5 | 9.5 | 6.5 |
| 3g | 91.9 | 120 | 91.0 | 45.5 | 71.0 | 25.3 | 1.4 | 1.8 | 0.5 | 10.83 | 5.95 | 3.0 | 18.1 | 7.1 |
| 3h | 96.7 | 120 | 95.0 | 47.5 | 86.3 | 7.7 | 1.0 | 1.5 | 4.7 | 4.88 | 2.22 | 1.1 | 7.7 | 7.1 |
| 3i | 58.9 | 75 | 59.4 | 47.5 | 90.4 | 1.8 | 0.5 | 0.9 | 6.4 | 2.66 | 0.42 | 0.3 | 3.6 | 7.1 |

EXAMPLE 4

In this example 0.33 grams of copper (II) hydroxide was employed. The silicon metal was 65×150 mesh particles. Solvent from a previous experiment was recycled (77.5 grms), and 22.2 grams of unused solvent was added to give 100 grams of solvent.

This run showed an 83.9 mole percent conversion of silicon metal to trimethoxysilane. In contrast, only 5.9 mole percent of the silicon metal was converted to tetramethoxysilane.

TABLE 5

| SAMPLE NO. | SAMPLE SIZE (GM) | SAMPLE INTERVAL TIME (MIN) | METHANOL FEED (GM) | METHANOL RATE (GM/H) | MEOH | TRI | TETR | SILOXANES | SOL | Si IN POT (GM) | Si/SAMPLE TOTAL (GM) | Si/SAMPLE RATE (GM/H) | SELECTIVITY SAMPLE | SELECTIVITY CUM |
|---|---|---|---|---|---|---|---|---|---|---|---|---|---|---|
| 5a | 44.5 | 60 | 45.1 | 45.1 | 58.3 | 35.2 | 4.3 | 1.6 | 0.6 | 50.00 | 4.11 | 4.1 | 8.2 | 8.2 |
| 5b | 49.1 | 60 | 45.9 | 45.9 | 30.7 | 66.0 | 2.4 | 1.0 | 0.0 | 45.89 | 7.77 | 7.8 | 27.5 | 15.5 |
| 5c | 100.3 | 123 | 98.9 | 48.2 | 27.2 | 68.8 | 2.8 | 1.1 | 0.0 | 38.12 | 16.61 | 8.1 | 24.6 | 19.8 |
| 5d | 46.8 | 60 | 47.5 | 47.5 | 35.8 | 56.7 | 4.9 | 2.0 | 0.6 | 21.51 | 6.73 | 6.7 | 11.6 | 17.5 |
| 5e | 96.8 | 120 | 91.0 | 45.5 | 53.2 | 41.2 | 2.6 | 1.6 | 1.4 | 14.78 | 9.97 | 5.0 | 15.8 | 17.1 |
| 5f | 101.3 | 120 | 95.0 | 47.5 | 78.7 | 9.2 | 1.0 | 1.1 | 11.1 | 4.81 | 2.58 | 1.3 | 9.2 | 16.4 |
| 5g | 99.6 | 120 | 87.1 | 43.6 | 89.9 | 1.4 | 0.1 | 0.3 | 8.3 | 2.23 | 0.41 | 0.2 | 14.0 | 16.4 |

TABLE 4

| SAMPLE NO. | SAMPLE SIZE (GM) | SAMPLE INTERVAL TIME (MIN) | METHANOL FEED (GM) | METHANOL RATE (GM/H) | MEOH | TRI | TETR | SILOXANES | SOL | Si IN POT (GM) | Si/SAMPLE TOTAL (GM) | Si/SAMPLE RATE (GM/H) | SELECTIVITY SAMPLE | SELECTIVITY CUM |
|---|---|---|---|---|---|---|---|---|---|---|---|---|---|---|
| 4a | 15.2 | 60 | 47.5 | 47.5 | 82.9 | 7.9 | 3.2 | 2.4 | 3.7 | 50.00 | 1.34 | 1.3 | 2.5 | 2.5 |
| 4b | 36.2 | 45 | 35.6 | 47.5 | 38.9 | 55.3 | 4.2 | 0.8 | 0.9 | 48.66 | 4.94 | 6.6 | 13.1 | 8.0 |
| 4c | 48.5 | 60 | 47.5 | 47.5 | 31.3 | 63.0 | 4.5 | 1.2 | 0.1 | 43.73 | 7.54 | 7.5 | 14.1 | 10.6 |
| 4d | 101.1 | 125 | 98.9 | 47.5 | 33.1 | 62.2 | 3.4 | 1.4 | 0.0 | 36.19 | 15.36 | 7.4 | 18.5 | 13.7 |
| 4e | 94.8 | 120 | 95.0 | 47.5 | 44.6 | 49.1 | 4.5 | 1.6 | 0.2 | 20.82 | 11.81 | 5.9 | 11.0 | 12.8 |
| 4f | 97.6 | 120 | 95.0 | 47.5 | 7.9 | 18.2 | 2.7 | 1.4 | 2.8 | 9.01 | 4.88 | 2.4 | 6.77 | 11.8 |
| 4g | 40.3 | 51 | 39.6 | 46.6 | 88.9 | 3.8 | 1.4 | 1.2 | 4.7 | 4.13 | 0.57 | 0.7 | 2.6 | 11.4 |

EXAMPLE 5

In this example 0.11 grams of copper (II) hydroxide was employed. The silicon metal was 65×150 mesh particles. Solvent from a previous experiment was recycled (82.0 grams), and 18.0 grams of unused solvent was added to give 100 grams of solvent. This run showed an 89.1 mole percent conversion of the silicon metal to trimethoxysilane. In contrast only 4.4 mole percent silicon metal was converted to tetramethoxysilane.

EXAMPLES 6 AND 7

Examples 6 and 7 demonstrate that silicon and copper (II) hydroxide can be added to the reaction zone to replace consumed starting material.

EXAMPLE 6

In this experiment 0.33 grams of copper (II) hydroxide was employed. The silicon metal was 65×150 mesh particles. The initial amount of silicon metal was 50 grams.

Three additions, each containing 20 grams of silicon and 0.13 grams of copper (II) hydroxide were made to the slurry after samples 6g, 6i and 6k were taken, as indicated by an asterisk on Table 6, below.

This run showed an 82.6 mole percent conversion of silicon metal to trimethoxysilane. In contrast only 9.3 mole percent silicon metal was converted to tetramethoxysilane.

TABLE 6

| SAMPLE NO. | SAMPLE TAKEN (GM) | RX TIME (MIN) | METHANOL FEED (GM) | METHANOL RATE (GM/H) | MEOH | TRI | TETR | SILOXANES | SOL | Si IN POT (GM) | Si/SAMPLE TOTAL (GM) | Si/SAMPLE RATE (GM/H) | SELECTIVITY SAMPLE | SELECTIVITY CUM |
|---|---|---|---|---|---|---|---|---|---|---|---|---|---|---|
| 6a | 40.4 | 60 | 43.5 | 43.5 | 98.5 | 0.1 | 0.1 | 0.3 | 1.0 | 50.00 | 0.04 | 0.0 | 1.0 | 1.0 |
| 6b | 40.5 | 60 | 41.2 | 41.2 | 96.2 | 1.0 | 0.2 | 0.3 | 1.4 | 49.96 | 0.22 | 0.2 | 9.5 | 6.7 |
| 6c | 35.9 | 60 | 38.0 | 38.0 | 95.0 | 3.3 | 0.2 | 0.4 | 1.1 | 49.74 | 0.32 | 0.3 | 16.5 | 10.3 |
| 6d | 34.6 | 60 | 35.6 | 35.6 | 85.5 | 12.1 | 0.4 | 0.6 | 1.4 | 49.42 | 1.03 | 1.0 | 30.3 | 18.6 |
| 6e | 38.9 | 60 | 39.6 | 39.6 | 73.2 | 24.2 | 1.3 | 1.1 | 0.2 | 48.38 | 2.35 | 2.4 | 18.6 | 18.6 |
| 6f | 43.4 | 60 | 43.5 | 43.5 | 53.9 | 42.7 | 2.4 | 1.0 | 0.1 | 46.03 | 4.54 | 4.5 | 17.8 | 18.2 |
| *6g | 86.9 | 120 | 83.1 | 41.6 | 46.7 | 51.1 | 1.6 | 0.7 | 0.0 | 41.49 | 10.59 | 5.3 | 31.9 | 24.0 |
| 6h | 85.8 | 120 | 83.1 | 41.6 | 50.9 | 43.0 | 5.3 | 0.8 | 0.0 | 50.90 | 9.46 | 4.7 | 8.1 | 14.8 |
| *6i | 40.9 | 60 | 41.9 | 41.9 | 50.5 | 44.6 | 4.3 | 0.6 | 0.0 | 41.44 | 4.57 | 4.6 | 10.4 | 14.0 |
| 6j | 83.1 | 120 | 79.1 | 39.6 | 52.2 | 40.6 | 6.7 | 0.5 | 0.0 | 56.87 | 8.86 | 4.4 | 6.1 | 11.1 |
| *6k | 42.1 | 60 | 40.4 | 40.4 | 58.0 | 36.0 | 5.1 | 0.9 | 0.0 | 48.01 | 3.96 | 4.0 | 7.1 | 10.6 |
| 6l | 82.4 | 120 | 82.3 | 41.2 | 60.0 | 32.0 | 7.7 | 0.3 | 0.0 | 64.05 | 7.28 | 3.6 | 4.2 | 8.8 |

TABLE 6-continued

| SAMPLE TAKEN (GM) | RX TIME (MIN) | METHANOL FEED (GM) | METHANOL RATE (GM/H) | GC ANALYSIS (%) MEOH | TRI | TETR | SILOXANES | SOL | Si IN POT (GM) | Si/SAMPLE TOTAL (GM) | Si/SAMPLE RATE (GM/H) | SELECTIVITY SAMPLE | SELECTIVITY CUM |
|---|---|---|---|---|---|---|---|---|---|---|---|---|---|
| 6m 43.6 | 60 | 37.2 | 37.2 | 51.5 | 12.7 | 35.0 | 0.8 | 0.0 | 56.77 | 4.16 | 4.2 | 0.4 | 5.5 |
| 6n 40.7 | 60 | 43.5 | 43.5 | 62.2 | 26.2 | 10.1 | 1.4 | 0.1 | 52.61 | 3.34 | 3.3 | 2.6 | 5.2 |
| 6o 42.1 | 60 | 41.9 | 41.9 | 52.7 | 43.4 | 3.2 | 0.7 | 0.0 | 49.27 | 4.51 | 4.5 | 13.6 | 5.5 |
| 6p 78.7 | 120 | 77.6 | 38.8 | 53.0 | 42.5 | 3.3 | 1.0 | 0.3 | 44.76 | 8.34 | 4.2 | 12.9 | 5.9 |
| D NO. | | | | | | | | | | | | | |
| 6q 78.1 | 120 | 76.8 | 38.4 | 60.7 | 35.0 | 2.9 | 1.1 | 0.3 | 36.43 | 6.89 | 3.4 | 12.1 | 6.2 |
| 6r 29.6 | 60 | 29.3 | 29.3 | 48.6 | 47.1 | 3.2 | 0.8 | 0.3 | 29.54 | 3.43 | 3.4 | 14.7 | 6.3 |
| 6s 46.7 | 60 | 43.5 | 43.5 | 61.9 | 31.3 | 5.7 | 1.0 | 0.1 | 26.11 | 3.95 | 4.0 | 5.5 | 6.3 |
| 6t 82.5 | 120 | 79.1 | 39.6 | 61.00 | 32.5 | 3.5 | 1.9 | 1.1 | 22.16 | 7.05 | 3.5 | 9.3 | 6.5 |
| 6u 79.5 | 120 | 77.6 | 38.8 | 68.4 | 24.6 | 3.8 | 1.8 | 1.4 | 15.11 | 5.37 | 2.7 | 6.5 | 6.5 |
| 6v 48.3 | 60 | 41.2 | 41.2 | 80.4 | 12.1 | 2.0 | 2.4 | 3.1 | 9.74 | 1.79 | 1.8 | 6.1 | 6.4 |
| 6w 52.3 | 90 | 51.4 | 34.3 | 86.1 | 6.1 | 1.2 | 2.2 | 4.4 | 7.95 | 1.11 | 0.7 | 5.1 | 6.4 |
| 6x 45.7 | 60 | 41.2 | 41.2 | 91.1 | 0.8 | 0.9 | 0.9 | 6.3 | 6.84 | 0.25 | 0.3 | 0.9 | 6.4 |
| 6y 33.5 | 60 | 32.4 | 32.4 | 92.3 | 0.5 | 0.2 | 0.6 | 6.4 | 6.58 | 0.10 | 0.1 | 2.5 | 6.4 |
| 6z 40.0 | 60 | 37.2 | 37.2 | 92.6 | 0.1 | 0.1 | 0.4 | 6.8 | 6.49 | 0.05 | 0.1 | 1.0 | 6.4 |

[*indicates addition of silicon metal and catalyst]

EXAMPLE 7

In this experiment 0.33 grams of copper (II) hydroxide was employed. The silicon metal was 65×150 mesh particles. The initial amount of silicon metal was 50 grams. Three additions, each containing 20 grams of silicon metal and 0.13 grams of copper (II) hydroxide were made to the slurry after sample 7d, 7h and 7k, as indicated by an asterisk in Table 7, below.

This run showed an 80.4 mole percent conversion of silicon metal to trimethoxysilane. In contrast only 9.6 mole percent silicon metal was converted to tetramethoxysilane.

That which is claimed is:
1. A process for producing trialkoxysilane of the formula HSi(OR)₃ wherein R is an alkyl group containing from 1 to 6 carbon atoms which comprises:

(a) forming a reaction mixture comprising an alcohol of the formula ROH wherein R is as defined above, an inert solvent, silicon metal, and a catalytically effective amount of copper (II) hydroxide; and
(b) reacting said alcohol with said silicon metal in the presence of said copper (II) hydroxide to produce the trialkoxysilane.

2. The process of claim 1, wherein R is an alkyl group containing from 1 to 3 carbon atoms.
3. The process of claim 2 wherein R is methyl.
4. The process of claim 2 wherein R is ethyl.
5. The process of claim 1 wherein the amount of copper (II) hydroxide catalyst is from about 0.01 to about 5 parts by weight per 100 parts by weight of silicon metal.

TABLE 7

| SAMPLE NO. | SAMPLE TAKEN (GM) | RX TIME (MIN) | METHANOL FEED (GM) | METHANOL RATE (GM/H) | GC ANALYSIS (%) MEOH | TRI | TETR | SILOXANES | SOL | Si IN POT (GM) | Si/SAMPLE TOTAL (GM) | Si/SAMPLE RATE (GM/H) | SELECTIVITY SAMPLE | SELECTIVITY CUM |
|---|---|---|---|---|---|---|---|---|---|---|---|---|---|---|
| 7a | 43.4 | 60 | 51.4 | 51.4 | 58.4 | 35.4 | 1.4 | 4.2 | 0.6 | 50.00 | 4.06 | 4.1 | 25.3 | 25.3 |
| 7b | 48.0 | 60 | 43.5 | 43.5 | 26.6 | 69.4 | 2.1 | 1.9 | 0.0 | 45.94 | 8.04 | 8.0 | 33.0 | 30.1 |
| 7c | 43.1 | 60 | 43.5 | 43.5 | 27.4 | 68.0 | 2.4 | 2.2 | 0.0 | 37.90 | 7.13 | 7.1 | 28.3 | 29.4 |
| *7d | 50.7 | 60 | 47.5 | 47.5 | 30.0 | 65.3 | 2.8 | 1.9 | 0.0 | 30.77 | 8.08 | 8.1 | 23.3 | 27.3 |
| 7e | 38.6 | 60 | 31.7 | 31.7 | 27.5 | 66.4 | 4.7 | 1.4 | 0.0 | 42.69 | 6.34 | 6.3 | 14.1 | 23.2 |
| 7f | 54.0 | 70 | 59.4 | 50.9 | 44.3 | 49.8 | 4.6 | 1.3 | 0.0 | 36.35 | 6.79 | 5.8 | 10.8 | 19.6 |
| 7g | 44.2 | 60 | 39.6 | 39.6 | 59.6 | 30.2 | 9.3 | 0.8 | 0.1 | 29.56 | 3.90 | 3.9 | 3.2 | 14.2 |
| *7h | 30.7 | 60 | 31.2 | 31.2 | 71.2 | 25.5 | 2.8 | 0.5 | 0.0 | 25.65 | 1.99 | 2.0 | 9.1 | 13.9 |
| 7i | 36.3 | 60 | 35.6 | 35.6 | 77.7 | 13.3 | 8.2 | 0.7 | 0.1 | 43.66 | 1.71 | 1.7 | 1.6 | 11.6 |
| 7j | 36.4 | 60 | 35.6 | 35.6 | 53.9 | 39.2 | 6.2 | 0.6 | 1.1 | 41.95 | 3.74 | 3.7 | 6.3 | 11.0 |
| *7k | 37.1 | 60 | 39.6 | 39.6 | 50.5 | 41.5 | 6.4 | 1.1 | 0.5 | 38.21 | 4.06 | 4.1 | 6.5 | 10.5 |
| 7l | 60.7 | 60 | 51.4 | 51.4 | 52.1 | 38.9 | 7.4 | 1.5 | 0.1 | 54.14 | 6.46 | 6.5 | 5.3 | 9.5 |
| 7m | 50.4 | 60 | 43.5 | 43.5 | 53.1 | 35.8 | 10.1 | 0.9 | 0.1 | 47.69 | 5.18 | 5.2 | 3.5 | 8.5 |
| 7n | 54.9 | 60 | 51.4 | 51.4 | 50.5 | 37.3 | 10.8 | 1.3 | 0.1 | 42.50 | 5.96 | 6.0 | 3.5 | 7.7 |
| 7o | 48.1 | 60 | 51.4 | 51.4 | 49.8 | 42.0 | 7.4 | 0.8 | 0.0 | 36.55 | 5.38 | 5.4 | 5.7 | 7.5 |
| 7p | 56.0 | 60 | 43.5 | 43.5 | 51.6 | 40.3 | 7.2 | 0.9 | 0.0 | 31.17 | 6.04 | 6.0 | 5.6 | 7.4 |
| 7q | 51.0 | 60 | 51.4 | 51.4 | 54.1 | 34.5 | 9.8 | 1.6 | 0.0 | 25.13 | 5.15 | 5.1 | 3.5 | 7.0 |
| 7r | 51.5 | 60 | 55.4 | 55.4 | 66.9 | 26.9 | 4.4 | 1.2 | 0.6 | 19.98 | 3.74 | 3.7 | 6.1 | 6.9 |
| 7s | 42.7 | 60 | 39.6 | 39.6 | 70.5 | 24.7 | 3.2 | 1.1 | 0.5 | 16.24 | 2.78 | 2.8 | 7.7 | 7.0 |
| 7t | 37.5 | 60 | 35.6 | 35.6 | 68.1 | 23.5 | 3.9 | 2.1 | 2.4 | 13.46 | 2.47 | 2.5 | 6.0 | 6.9 |
| 7u | 41.2 | 60 | 31.7 | 31.7 | 71.7 | 17.2 | 3.7 | 2.8 | 4.6 | 10.99 | 2.17 | 2.2 | 4.6 | 6.9 |
| 7v | 48.7 | 60 | 51.4 | 51.4 | 83.5 | 6.8 | 2.1 | 2.5 | 5.1 | 8.82 | 1.23 | 1.2 | 3.2 | 6.8 |
| 7w | 48.6 | 60 | 39.6 | 39.6 | 89.6 | 1.7 | 0.5 | 0.9 | 7.3 | 7.59 | 0.33 | 0.3 | 3.4 | 6.8 |
| 7x | 40.7 | 60 | 35.6 | 35.6 | 88.7 | 0.2 | 0.2 | 0.7 | 10.2 | 7.26 | 0.10 | 0.1 | 1.0 | 6.8 |
| 7y | 16.8 | 71 | 15.9 | 13.4 | 99.3 | 0.1 | 0.4 | 0.1 | 0.1 | 7.16 | 0.02 | 0.0 | 0.3 | 6.8 |
| 7z | 58.8 | 70 | 63.5 | 54.4 | 95.2 | 0.1 | 0.1 | 0.4 | 4.2 | 7.14 | 0.08 | 0.1 | 1.0 | 6.8 |
| 7aa | 40.9 | 50 | 39.7 | 47.6 | 96.2 | 0.1 | 0.0 | 0.1 | 3.5 | 7.06 | 0.02 | 0.0 | 1.3 | 6.8 |

[*indicates addition of silicon metal and catalyst]

6. The process of claim 1 wherein the amount of copper (II) hydroxide is from about 0.1 to about 2.6 parts by weight per 100 parts by weight of silicon metal.

7. The process of claim 1 wherein the amount of copper (II) hydroxide is from about 0.1 to about 0.7 parts by weight per 100 parts by weight of silicon metal.

8. The process of claim 1 wherein the reaction mixture is agitated during the reaction.

9. The process of claim 1 wherein the temperature is maintained above about 150° C. during the reaction.

10. The process of claim 9, wherein the temperature is maintained in the range of about 200° C. to about 240° C.

11. The process of claim 1 wherein additional amounts of silicon metal are subsequently fed to the reaction to replace silicon metal consumed.

12. A process for producing trimethoxysilane, HSi(OCH$_3$)$_3$, which comprises:
 (a) forming a reaction mixture comprising methanol, an inert solvent, silicon metal and a catalytically effective amount of copper(II) hydroxide; and
 (b) reacting said methanol with said silicon metal in the presence of the copper (II) hydroxide to produce trimethoxysilane.

13. The process of claim 12 wherein the amount of copper (II) hydroxide catalyst is from about 0.01 to about 5 parts by weight per 100 parts by weight of silicon metal.

14. The process of claim 13 wherein the amount of copper (II) hydroxide is from about 0.1 to about 2.6 parts by weight per 100 parts by weight of silicon metal.

15. The process of claim 14 wherein the amount of copper (II) hydroxide is from about 0.1 to about 0.7 parts by weight per 100 parts by weight of silicon metal.

16. The process of claim 12 wherein the reaction mixture is agitated during step (b).

17. The process of claim 12 wherein the temperature of the reaction zone is maintained above about 150° C. during step (b).

18. The process of claim 17 wherein the temperature of the reaction zone is maintained in the range of about 200° C. to about 240° C.

19. The process of claim 18, wherein additional amounts of silicon metal are added to the reaction zone to replace silicon metal consumed by the reaction.

* * * * *